United States Patent
Berthon-Jones

(10) Patent No.: US 6,279,569 B1
(45) Date of Patent: Aug. 28, 2001

(54) DETERMINATION OF LEAK AND RESPIRATORY AIRFLOW

(75) Inventor: Michael Berthon-Jones, Leonay (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/525,042

(22) Filed: Mar. 14, 2000

Related U.S. Application Data

(63) Continuation of application No. 08/911,513, filed on Aug. 14, 1997, now Pat. No. 6,152,129.

(30) Foreign Application Priority Data

Aug. 14, 1996 (AU) .................................................. PO1638

(51) Int. Cl.[7] .................................................. A61M 15/00
(52) U.S. Cl. ................................. 128/200.24; 128/204.23
(58) Field of Search ........................ 128/204.18, 204.21, 128/204.23, 204.26, 205.23, 200.24, 203.12, 207.14

(56) References Cited

U.S. PATENT DOCUMENTS

| | | |
|---|---|---|
| Re. 35,295 | 7/1996 | Estes et al. . |
| Re. 35,339 | 10/1996 | Rapoport . |
| 2,904,033 | 9/1959 | Shane . |
| 3,099,985 | 8/1963 | Wilson et al. . |
| 3,502,100 | 3/1970 | Jonson . |
| 3,559,638 | 2/1971 | Potter . |
| 3,595,228 | 7/1971 | Simon et al. . |
| 3,611,801 | 10/1971 | Paine et al. . |

(List continued on next page.)

FOREIGN PATENT DOCUMENTS

| | | |
|---|---|---|
| B-59270/90 | 12/1990 | (AU) . |
| A-62221/90 | 3/1991 | (AU) . |
| A-76019/91 | 1/1992 | (AU) . |
| A-33877/93 | 4/1993 | (AU) . |
| A-38508/93 | 7/1993 | (AU) . |
| A-48748/93 | 9/1993 | (AU) . |
| A-48748/93 | 12/1993 | (AU) . |
| A-52628/93 | 7/1994 | (AU) . |

(List continued on next page.)

OTHER PUBLICATIONS

New! Breas PV 100 CPAP First Class Quality and Function. At the right Price; Jul. 4, 1998, pp 1–2.
PV 101 Bi Level CPAP and PV 102 Bi–Level Time; pp 1–3, Dec. 10, 1998.
Prodigy Medical Supplies Co. Ltd.; CPAP.
Puritan Bennett; Companion 318 Nasal CPAP System; 5/1993.
Nellcor Puritan Bennett; Announcing the Goodnight 314 and GoodKnight 318 Nasal CPAP Systems, 1996.

(List continued on next page.)

Primary Examiner—Aaron J. Lewis
Assistant Examiner—Teena Mitchell
(74) Attorney, Agent, or Firm—Gottlieb, Rackman & Reisman, PC

(57) ABSTRACT

Methods and apparatus for determining leak and respiratory airflow are disclosed. A pressure sensor (34) and a differential pressure sensor (32) have connection with a pneumotach (24) to derive instantaneous mask pressure and airflow respectively. A microcontroller (38) estimates a non-linear conductance of any leak path occurring at a mask (12) as being the low pass filtered instantaneous airflow divided by the low pass filtered square root of the instantaneous pressure. The instantaneous leak flow is then the conductance multiplied by the square root of the instantaneous pressure, and the respiratory airflow is calculated as being the instantaneous airflow minus the instantaneous leak flow. The time constants for the low pass filtering performed by the microcontroller (38) can be dynamically adjusted dependent upon sudden changes in the instantaneous leak flow.

33 Claims, 10 Drawing Sheets

U.S. PATENT DOCUMENTS

| | | |
|---|---|---|
| 3,726,270 | 4/1973 | Griffis et al. . |
| 3,741,208 | 6/1973 | Jonsson et al. . |
| 3,783,893 | 1/1974 | Davison . |
| 3,802,417 | 4/1974 | Lang . |
| 3,817,246 | 6/1974 | Weigl . |
| 3,882,847 | 5/1975 | Jacobs . |
| 3,903,875 | 9/1975 | Hughes . |
| 3,914,994 | 10/1975 | Banner . |
| 3,932,054 | 1/1976 | McKelvey . |
| 3,985,467 | 10/1976 | Lefferson . |
| 3,989,037 | 11/1976 | Franetzki . |
| 3,992,598 | 11/1976 | Welsh et al. . |
| 3,995,661 | 12/1976 | Van Fossen . |
| 4,006,634 | 2/1977 | Billette et al. . |
| 4,083,245 | 4/1978 | Osborn . |
| 4,109,749 | 8/1978 | Sweet . |
| 4,119,096 | 10/1978 | Drews . |
| 4,206,754 | 6/1980 | Cox et al. . |
| 4,249,527 | 2/1981 | Ko et al. . |
| 4,301,833 | 11/1981 | Donald, III . |
| 4,312,235 | 1/1982 | Daigle . |
| 4,320,766 | 3/1982 | Alihanka et al. . |
| 4,322,594 | 3/1982 | Brissou . |
| 4,381,788 | 5/1983 | Douglas . |
| 4,387,722 | 6/1983 | Kearns . |
| 4,396,034 | 8/1983 | Cherniak . |
| 4,414,982 | 11/1983 | Durkan . |
| 4,433,693 | 2/1984 | Hochstein . |
| 4,448,058 | 5/1984 | Jaffe et al. . |
| 4,449,525 | 5/1984 | White et al. . |
| 4,481,944 | 11/1984 | Bunnell . |
| 4,499,914 | 2/1985 | Schebler . |
| 4,506,666 | 3/1985 | Durkan . |
| 4,519,399 | 5/1985 | Hori . |
| 4,530,334 | 7/1985 | Pagdin . |
| 4,550,615 | 11/1985 | Grant . |
| 4,550,726 | 11/1985 | McEwen . |
| 4,558,710 | 12/1985 | Eichler . |
| 4,570,631 | 2/1986 | Durkan . |
| 4,576,179 | 3/1986 | Manus et al. . |
| 4,579,114 | 4/1986 | Gray et al. . |
| 4,580,575 | 4/1986 | Birnbaum et al. . |
| 4,592,880 | 6/1986 | Murakami . |
| 4,595,016 | 6/1986 | Fertig et al. . |
| 4,602,644 | 7/1986 | DiBenedetto et al. . |
| 4,630,614 | 12/1986 | Atlas . |
| 4,648,396 | 3/1987 | Raemer . |
| 4,648,407 | 3/1987 | Sackner . |
| 4,655,213 | 4/1987 | Rapoport et al. . |
| 4,677,975 | 7/1987 | Edgar et al. . |
| 4,686,974 | 8/1987 | Sato et al. . |
| 4,686,999 | 8/1987 | Snyder et al. . |
| 4,738,266 | 4/1988 | Thatcher . |
| 4,747,403 | 5/1988 | Gluck et al. . |
| 4,773,411 | 9/1988 | Downs . |
| 4,777,963 | 10/1988 | McKenna . |
| 4,795,314 | 1/1989 | Prybella et al. . |
| 4,802,485 | 2/1989 | Bowers et al. . |
| 4,803,471 | 2/1989 | Rowland . |
| 4,819,629 | 4/1989 | Jonson . |
| 4,823,788 | 4/1989 | Smith et al. . |
| 4,825,802 | 5/1989 | Le Bec . |
| 4,827,922 | 5/1989 | Champain et al. . |
| 4,838,258 | 6/1989 | Dryden et al. . |
| 4,844,085 | 7/1989 | Gattinoni . |
| 4,856,506 | 8/1989 | Jinotti . |
| 4,870,960 | 10/1989 | Hradek . |
| 4,870,963 | 10/1989 | Carter . |
| 4,887,607 | 12/1989 | Beatty . |
| 4,913,401 | 4/1990 | Handke . |
| 4,915,103 | 4/1990 | Visveshwara et al. . |
| 4,928,684 | 5/1990 | Breitenfelder et al. . |
| 4,938,210 | 7/1990 | Shene . |
| 4,938,212 | 7/1990 | Snook et al. . |
| 4,944,310 | 7/1990 | Sullivan . |
| 4,957,107 | 9/1990 | Sipin . |
| 4,960,118 | 10/1990 | Pennock . |
| 4,971,065 | 11/1990 | Pearce . |
| 4,972,842 | 11/1990 | Korten et al. . |
| 4,982,738 | 1/1991 | Griebel . |
| 4,986,269 | 1/1991 | Hakkinen . |
| 4,989,599 | 2/1991 | Carter . |
| 5,009,635 | 4/1991 | Scarberry . |
| 5,024,219 | 6/1991 | Dietz . |
| 5,046,491 | 9/1991 | Derrick . |
| 5,048,515 | 9/1991 | Sanso . |
| 5,052,400 | 10/1991 | Dietz . |
| 5,063,922 | 11/1991 | Hakkinen . |
| 5,063,938 | 11/1991 | Beck et al. . |
| 5,065,756 | 11/1991 | Rapoport . |
| 5,069,222 | 12/1991 | McDonald, Jr. . |
| 5,090,248 | 2/1992 | Cimmino et al. . |
| 5,099,837 | 3/1992 | Russel, Sr. et al. . |
| 5,105,354 | 4/1992 | Nishimura . |
| 5,107,830 | 4/1992 | Younes . |
| 5,107,831 | 4/1992 | Halpern et al. . |
| 5,117,819 | 6/1992 | Servidio et al. . |
| 5,129,390 | 7/1992 | Chopin et al. . |
| 5,134,995 | 8/1992 | Gruenke et al. . |
| 5,148,802 | 9/1992 | Sanders et al. . |
| 5,161,525 | 11/1992 | Kimm et al. . |
| 5,161,541 | 11/1992 | Bowman et al. . |
| 5,165,398 | 11/1992 | Bird . |
| 5,170,798 | 12/1992 | Riker . |
| 5,174,287 | 12/1992 | Kallok et al. . |
| 5,178,138 | 1/1993 | Walstrom et al. . |
| 5,183,983 | 2/1993 | Knop . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,230,330 | 7/1993 | Price . |
| 5,231,979 | 8/1993 | Rose et al. . |
| 5,231,983 | 8/1993 | Matson et al. . |
| 5,233,983 | 8/1993 | Markowitz . |
| 5,239,994 | 8/1993 | Atkins . |
| 5,239,995 | 8/1993 | Estes et al. . |
| 5,245,995 | 9/1993 | Sullivan et al. . |
| 5,259,373 | 11/1993 | Gruenke et al. . |
| 5,271,391 | 12/1993 | Graves . |
| 5,280,784 | 1/1994 | Kohler . |
| 5,293,864 | 3/1994 | McFadden . |
| 5,295,491 | 3/1994 | Gevins . |
| 5,303,698 | 8/1994 | Tobia et al. . |
| 5,303,700 | 4/1994 | Weismann et al. . |
| 5,305,787 | 4/1994 | Thygesen . |
| 5,311,875 | 5/1994 | Stasz . |
| 5,313,937 | 5/1994 | Zdrojkowski . |
| 5,322,057 | 6/1994 | Raabe et al. . |
| 5,327,899 | 7/1994 | Harris et al. . |
| 5,335,654 | 8/1994 | Rapoport . |
| 5,335,656 | 8/1994 | Bowe et al. . |
| 5,343,878 | 9/1994 | Scarberry et al. . |
| 5,353,788 | 10/1994 | Miles . |
| 5,360,008 | 11/1994 | Campbell, Jr. . |
| 5,373,842 | 12/1994 | Olsson et al. . |
| 5,388,571 | 2/1995 | Roberts et al. . |
| 5,394,882 | 3/1995 | Mawhinney . |
| 5,398,673 | 3/1995 | Lambert . |
| 5,400,777 | 3/1995 | Olsson et al. . |
| 5,404,871 | 4/1995 | Goodman et al. . |

| | | |
|---|---|---|
| 5,413,111 | 5/1995 | Wilkinson . |
| 5,433,193 | 7/1995 | Sanders et al. . |
| 5,438,980 | 8/1995 | Phillips . |
| 5,443,061 | 8/1995 | Champain et al. . |
| 5,443,075 | 8/1995 | Holscher . |
| 5,448,996 | 9/1995 | Bellin et al. . |
| 5,458,137 | 10/1995 | Axe et al. . |
| 5,479,920 | 1/1996 | Piper et al. . |
| 5,479,939 | 1/1996 | Ogino . |
| 5,483,969 | 1/1996 | Testerman et al. . |
| 5,490,502 | 2/1996 | Rapoport et al. . |
| 5,492,113 | 2/1996 | Estes et al. . |
| 5,503,146 | 4/1996 | Froehlich et al. . |
| 5,507,282 | 4/1996 | Younes . |
| 5,509,404 | 4/1996 | Lloyd et al. . |
| 5,509,414 | 4/1996 | Hok . |
| 5,513,631 | 5/1996 | McWilliams . |
| 5,517,983 | 5/1996 | Deighan et al. . |
| 5,522,382 | 6/1996 | Sullivan et al. . |
| 5,526,805 | 6/1996 | Lutz et al. . |
| 5,535,738 | 7/1996 | Estes et al. . |
| 5,535,739 | 7/1996 | Rapoport et al. . |
| 5,537,997 | 7/1996 | Mechlenburg et al. . |
| 5,540,219 | 7/1996 | Mechlenburg et al. . |
| 5,540,220 | 7/1996 | Gropper . |
| 5,540,733 | 7/1996 | Testerman et al. . |
| 5,546,655 | 8/1996 | Erickson . |
| 5,546,933 | 8/1996 | Rapoport et al. . |
| 5,546,952 | 8/1996 | Erickson . |
| 5,549,106 | 8/1996 | Gruenke et al. . |
| 5,551,418 | 9/1996 | Estes et al. . |
| 5,551,419 | 9/1996 | Froehlich et al. . |
| 5,558,099 | 9/1996 | Bowman et al. . |
| 5,567,127 | 10/1996 | Wentz . |
| 5,570,682 | 11/1996 | Johnson . |
| 5,588,439 | 12/1996 | Hollub . |
| 5,590,648 | 1/1997 | Mitchell . |
| 5,598,838 | 2/1997 | Servidio et al. . |
| 5,605,151 | 2/1997 | Lynn . |
| 5,608,647 | 3/1997 | Rubsamen et al. . |
| 5,617,846 | 4/1997 | Graetz et al. . |
| 5,630,411 | 5/1997 | Holscher . |
| 5,632,269 | 5/1997 | Zdrojkowski . |
| 5,633,552 | 5/1997 | Lee et al. . |
| 5,642,730 | 7/1997 | Bosom . |
| 5,645,053 | 7/1997 | Remmers et al. . |
| 5,647,351 | 7/1997 | Weismann et al. . |
| 5,655,520 | 8/1997 | Howe et al. . |
| 5,655,522 | 8/1997 | Mechlenburg et al. . |
| 5,660,171 | 8/1997 | Kimm et al. . |
| 5,666,946 | 9/1997 | Langenback . |
| 5,682,878 | 11/1997 | Ogden . |
| 5,685,296 | 11/1997 | Zdrojkowski et al. . |
| 5,701,883 | 12/1997 | Hete et al. . |
| 5,704,345 | 1/1998 | Berthon-Jones . |
| 5,715,812 | 2/1998 | Deighan et al. . |
| 5,730,119 | 3/1998 | Lekholm . |
| 5,730,121 | 3/1998 | Hawkins . |
| 5,740,795 | 4/1998 | Brydon . |
| 5,740,796 | 4/1998 | Skog . |
| 5,743,253 | 4/1998 | Castor et al. . |
| 5,794,615 | 8/1998 | Estes . |
| 5,797,852 | 8/1998 | Karakasoglu et al. . |
| 5,803,066 | 9/1998 | Rapoport et al. . |
| 5,823,187 | 10/1998 | Estes et al. . |
| 5,845,636 | 12/1998 | Gruenke et al. . |
| 5,970,975 * | 10/1999 | Estes et al. ............... 128/204.23 |
| 6,029,664 * | 2/2000 | Zdrojkowski et al. ........ 128/204.23 |
| 6,105,575 * | 8/2000 | Estes et al. ............... 128/204.23 |

FOREIGN PATENT DOCUMENTS

| | | |
|---|---|---|
| B 79174/94 | 6/1995 | (AU) . |
| A-34471/95 | 2/1996 | (AU) . |
| A-40711-95 | 4/1996 | (AU) . |
| B 34354/95 | 5/1996 | (AU) . |
| A 39130/95 | 6/1996 | (AU) . |
| 459104 | 4/1928 | (DE) . |
| 3015279 A1 | 10/1981 | (DE) . |
| 34 02 603 A1 | 1/1984 | (DE) . |
| 3345067 A1 | 6/1984 | (DE) . |
| 3429345 A1 | 6/1985 | (DE) . |
| 34 02 603 A1 | 8/1985 | (DE) . |
| 3537507 A1 | 4/1987 | (DE) . |
| 3539073 A1 | 5/1987 | (DE) . |
| 4432219 C1 | 4/1996 | (DE) . |
| 296 12 119 U1 | 12/1996 | (DE) . |
| 195 36 632 A | 3/1997 | (DE) . |
| 0 062 166 A2 | 10/1982 | (EP) . |
| 0 066 451 A1 | 12/1982 | (EP) . |
| B1 0 088 761 | 9/1983 | (EP) . |
| 0 164 500 A2 | 3/1985 | (EP) . |
| 0 171 321 A1 | 2/1986 | (EP) . |
| 0 185 980 | 7/1986 | (EP) . |
| 0 236 850 A2 | 9/1987 | (EP) . |
| 298 367 A2 | 1/1989 | (EP) . |
| 0 425 092 A1 | 9/1989 | (EP) . |
| 0 452 001 A2 | 3/1990 | (EP) . |
| 0 388 525 A1 | 9/1990 | (EP) . |
| 0 425 092 A1 | 5/1991 | (EP) . |
| 0 461 281 A1 | 12/1991 | (EP) . |
| 481 459 A1 | 4/1992 | (EP) . |
| 0 062 166 A2 | 10/1992 | (EP) . |
| 0514 744 | 11/1992 | (EP) . |
| 549299 A2 | 6/1993 | (EP) . |
| 606 687 A2 | 7/1994 | (EP) . |
| 0705615 A1 | 9/1994 | (EP) . |
| 0651971 A1 | 5/1995 | (EP) . |
| 0 656 216 A2 | 6/1995 | (EP) . |
| 0661 071 A1 | 7/1995 | (EP) . |
| 178 925 A2 | 4/1996 | (EP) . |
| 0709107A1 | 5/1996 | (EP) . |
| 0 714 670 A2 | 6/1996 | (EP) . |
| 0 765 631 A2 | 4/1997 | (EP) . |
| 0 788 805 A2 | 8/1997 | (EP) . |
| 0 839 545 A1 | 5/1998 | (EP) . |
| 0 872 643 A2 | 10/1998 | (EP) . |
| 2 574 657 A1 | 6/1986 | (FR) . |
| 2 672 221 A1 | 8/1992 | (FR) . |
| 2682042 A1 | 4/1993 | (FR) . |
| 1432572 | 4/1976 | (GB) . |
| 1 444 053 | 7/1976 | (GB) . |
| 1583273 | 1/1981 | (GB) . |
| 2 077 444 | 12/1981 | (GB) . |
| 2 147 506 A | 5/1985 | (GB) . |
| 2 164 569 A | 3/1986 | (GB) . |
| 2 166 871 A | 5/1986 | (GB) . |
| 2 205 167 A | 11/1988 | (GB) . |
| 2 221 302 A | 1/1990 | (GB) . |
| 2 254 700 A | 10/1992 | (GB) . |
| 2 261 290 A | 5/1993 | (GB) . |
| 2 271 811 A | 4/1994 | (GB) . |
| 2 294 400 A | 5/1996 | (GB) . |
| 54-104369 | 8/1979 | (JP) . |
| 60/212607 | 4/1984 | (JP) . |
| 60-212607 | 10/1985 | (JP) . |
| 62-103297 | 4/1987 | (JP) . |
| 63-275352 | 11/1988 | (JP) . |
| 2-173397 | 12/1988 | (JP) . |
| 4-70516 A | 3/1992 | (JP) . |
| 06249739A | 9/1994 | (JP) . |

| | | |
|---|---|---|
| 06249740A | 9/1994 | (JP) . |
| 06249741A | 9/1994 | (JP) . |
| 6-249742A | 9/1994 | (JP) . |
| 6-249743A | 9/1994 | (JP) . |
| 6-249744A | 9/1994 | (JP) . |
| 07280609 A | 10/1995 | (JP) . |
| 8019610 A | 1/1996 | (JP) . |
| 2012848 C1 | 5/1994 | (RU) . |
| SU 1710064 A1 | 2/1992 | (SE) . |
| 467041 B | 5/1992 | (SE) . |
| SU 1710064 A1 | 2/1994 | (SE) . |
| WO 80/01044 | 5/1980 | (WO) . |
| WO 82/03326 | 10/1982 | (WO) . |
| WO 82/03548 | 10/1982 | (WO) . |
| WO 86/05965 | 10/1986 | (WO) . |
| WO 86/06969 | 12/1986 | (WO) . |
| WO 87/02577 | 5/1987 | (WO) . |
| WO 89/09565 | 10/1988 | (WO) . |
| WO 88/10108 | 12/1988 | (WO) . |
| WO 90/14121 | 1/1990 | (WO) . |
| WO 90/09146 | 8/1990 | (WO) . |
| WO 90/14121 | 11/1990 | (WO) . |
| WO 91/12051 | 8/1991 | (WO) . |
| WO 91/19456 | 12/1991 | (WO) . |
| WO 92/11054 | 7/1992 | (WO) . |
| WO 92/15353 | 9/1992 | (WO) . |
| WO 92/22244 | 12/1992 | (WO) . |
| WO 93/08857 | 5/1993 | (WO) . |
| WO 93/09834 | 5/1993 | (WO) . |
| WO 93/21982 | 11/1993 | (WO) . |
| WO 93/24169 | 12/1993 | (WO) . |
| WO 94/04071 | 3/1994 | (WO) . |
| WO 94/16759 | 8/1994 | (WO) . |
| WO 94/20018 | 9/1994 | (WO) . |
| WO 94/20051 | 9/1994 | (WO) . |
| WO 94/22517 | 10/1994 | (WO) . |
| WO 94/23780 | 10/1994 | (WO) . |
| WO 95/32016 | 11/1995 | (WO) . |
| WO 95/34917 | 12/1995 | (WO) . |
| WO 96/16688 | 6/1996 | (WO) . |
| WO 96/32055 | 10/1996 | (WO) . |
| WO 96/36279 | 11/1996 | (WO) . |
| WO 96/40337 | 12/1996 | (WO) . |
| WO 96/41571 | 12/1996 | (WO) . |
| WO 97/02064 | 1/1997 | (WO) . |
| WO 97/05824 | 2/1997 | (WO) . |
| WO 97/10019 | 3/1997 | (WO) . |
| WO 97/14354 | 4/1997 | (WO) . |
| WO 97/15343 | 5/1997 | (WO) . |
| WO 97/18752 | 5/1997 | (WO) . |
| WO 97/20499 | 6/1997 | (WO) . |
| WO 97/22377 | 6/1997 | (WO) . |
| WO 97/28838 | 8/1997 | (WO) . |
| WO 97/41812 | 11/1997 | (WO) . |
| WO 98/06449 | 2/1998 | (WO) . |
| WO 98/25662 | 6/1998 | (WO) . |
| WO 98/33433 | 8/1998 | (WO) . |
| WO 98/35715 | 8/1998 | (WO) . |
| WO 98/36245 | 8/1998 | (WO) . |
| WO 98/36338 | 8/1998 | (WO) . |
| WO 98/47554 | 10/1998 | (WO) . |
| WO 98/52467 | 11/1998 | (WO) . |
| WO 98/57691 | 12/1998 | (WO) . |

OTHER PUBLICATIONS

Puritan Bennett; Clean, Quiet, and Comfortable . . . The Companion's 515 Nasal CPAP System; 6/88.

DeVilbiss Night Guard Nasal CPAP for the Treatment of Obstructive Sleep Apnea.

Sunrise; DeVilbiss Horizon LT 8001 Nasal CPAP Therapy Small in Size, big on Features; 8/97.

Devilbiss; Revitalizer Soft Start; The Facts Speak for Themselves, 1992.

Tranquility; Performance CPAP Advantage.

Healthdyne International; Tranquility Plus.

Respironics Inc.; Respironics' Solo CPAP System Provides Simplified OSA Therapy at an Outstanding value; Sep. 19, 1996.

Respironics Inc.; The First Family of OSA Therapy; 1991

Fisher & Paykel Healthcare; HC200 Series Nasal CPAP Blower & Heated Humidifier.

Pierre Medical; Morphee Plus appareil de traitment des apnees du sommeil manuel d'utilisation.

Weinmann:Hamburg; Somnotron nCPAP–Gerat WM 23000, 11/91.

Puritan Bennett; 515a Part of Our Blueprint for the Future; 03/90.

Puritan Bennett; Companion 320 I/E Bi–Level Respiratory System; 4/93.

ResMed; Sullivan VPAP II & II ST.

ResMed; The Sullivan V Family of CPAP Systems; 1996.

ResMed; The Autoset Portable II; 1997.

ResMed; Sullivan Nasal CPAP System.

ResMed; The Sullivan IIID; 1995.

ResMed; The Sullivan Comfort; 1996.

DeVilbiss a Division of Sunrise Medical; Expand your Horizons With The Horizons; 1995.

Healthdyne Technologies; Home Health Care Dealer; The Journal of Home Medical Equipment and Services/Supplier; Nov. and Dec. 1997.

Healthdyne International; Tranquility Quest, The Compact CPAP for Greater patient comfort.

Airstep; Medical Products . . . Stand the Test of Time.

MAP Medical Progress for Physician und Patient; The Gentle Therapy for Sleep–Related Breathing Disorders.

Taema; Ventilation CP 90, 5/95.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Feel Well, Sensitive Sleep Apnea Therapy with Somnotron 3 and Somno–Mask System.

Respironics Inc.; Aria CPAP System; 1993.

Respironics Inc.; SleepEasy III A New Dawn in Patient Compliance.

Respironics Inc.; Multiple Choice REMstar Choice Nasal CPAP Systems, 1993.

MaxII nCPAP and Moritz II Bi–Level Brochure.

Derwent: Flowmeter for fluids–has turbine transducer and volumetric sensor for simultaneous calibration, 1995.

Mark Kantrowitz, Erik Horskotte and Cliff Joslyn, "Answers to Frequently Asked Questions About Fuzzy Logic and Fuzz Expert System", Version 1.24, last modified Feb. 20, 1996.

* cited by examiner

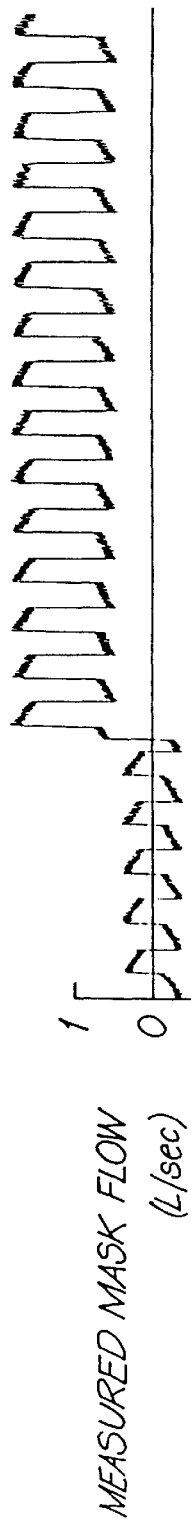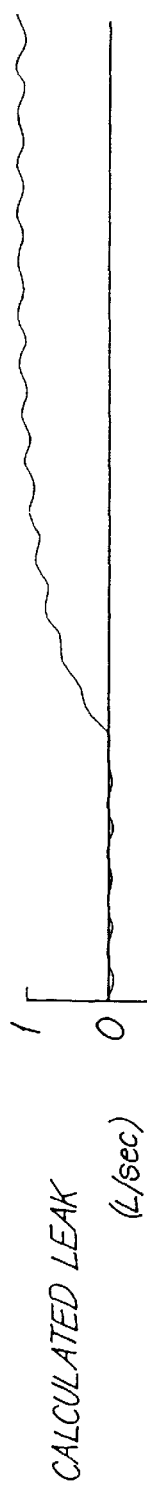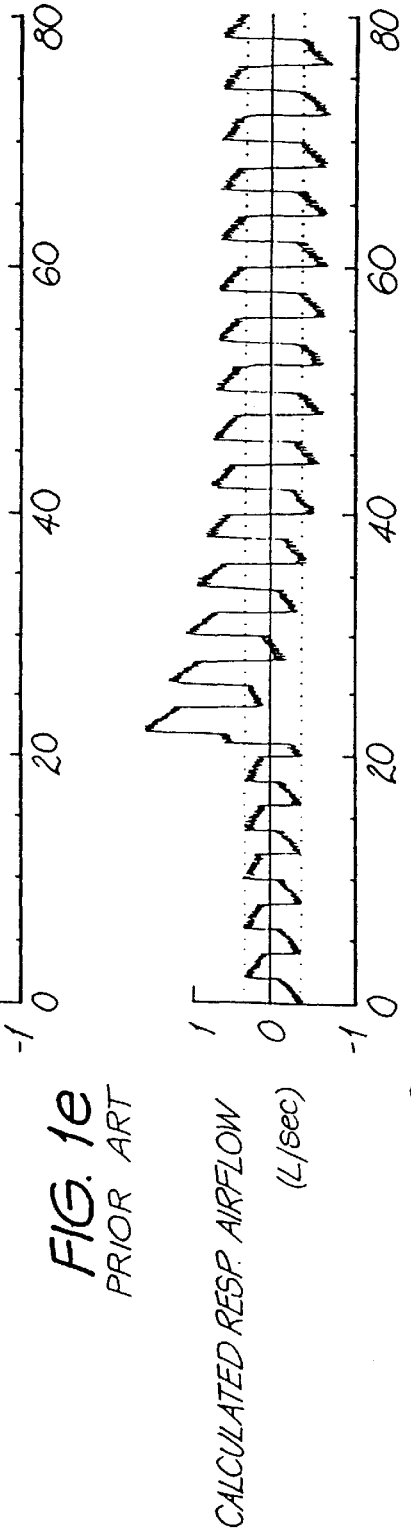
FIG. 1d PRIOR ART
FIG. 1e PRIOR ART
FIG. 1f PRIOR ART TRUE MASK PRESSURE (cmH2O)

TRUE RESPIRATORY AIRFLOW (L/sec)

TRUE MASK LEAK (L/sec)

MEASURED MASK FLOW $f_d$ (L/sec)

DETERMINATION OF LEAK AND RESPIRATORY AIRFLOW

This Application is a Continuation Application of U.S. patent application Ser. No. 08/911,513 for DETERMINATION OF LEAK AND RESPIRATORY AIRFLOW, filed Aug. 14, 1997, now U.S. Pat. No. 6,152,129.

FIELD OF THE INVENTION

The invention relates to methods and apparatus for the determination of leakage airflow and true respiratory airflow, particularly during mechanical ventilation.

The airflow determination can be for a subject who is either spontaneously or non-spontaneously breathing, or moves between these breathing states. The invention is especially suitable for, but not limited to, normally conscious and spontaneously breathing human subjects requiring long term ventilatory assistance, particularly during sleep.

BACKGROUND OF THE INVENTION

In this specification any reference to a "mask" is to be understood as including all forms of devices for passing breathable gas to a person's airway, including nose masks, nose and mouth masks, nasal prongs/pillows and endotracheal or tracheostomy tubes.

During mechanical ventilation, breathable gas is supplied for example via a mask, at a pressure which is higher during inspiration and lower during expiration. It is useful to measure the subject's respiratory airflow during mechanical ventilation to assess adequacy of treatment, or to control the operation of the ventilator.

Respiratory airflow is commonly measured with a pneumotachograph placed in the gas delivery path between the mask and the ventilator. Leaks between the mask and the subject are unavoidable. The pneumotachograph measures the sum of the respiratory airflow plus the flow through the leak. If the instantaneous flow through the leak is known, the respiratory airflow can be calculated by subtracting the flow through the leak from the flow at the pneumotach.

Known methods to correct for the flow through the leak assume (i) that the leak is substantially constant, and (ii) that over a sufficiently long time, inspiratory and expiratory respiratory airflow will cancel. If these assumptions are met, the average flow through the pneumotach over a sufficiently long period will equal the magnitude of the leak, and the true respiratory airflow may then be calculated as described.

The known method is only correct if the pressure at the mask is constant. If the mask pressure varies with time (for example, in the case of a ventilator), assumption (i) above will be invalid, and the calculated respiratory airflow will therefore be incorrect. This is shown markedly in FIGS. 1a–1f.

FIG. 1a shows a trace of measured mask pressure in bi-level CPAP treatment between about 4 cm $H_2O$ on expiration and 12 cm $H_2O$ on inspiration. FIG. 1b shows a trace of true respiratory airflow in synchronism with the mask pressure. At time=21 seconds a mask leak occurs, resulting in a leakage flow from the leak that is a function of the treatment pressure, as shown in FIG. 1c. The measured mask flow shown in FIG. 1d now includes an offset due to the leak flow. The prior art method then determines the calculated leak flow over a number of breaths, as shown in FIG. 1e. The resulting calculated respiratory flow, as the measured flow minus the calculating leak flow is shown in FIG. 1f, having returned to the correct mean value, however is incorrectly scaled in magnitude, giving a false indication of peak positive and negative airflow.

Another prior art arrangement is disclosed in European Publication No. 0 714 670 A2, including a calculation of a pressure-dependent leak component. The methodology relies on knowing precisely the occurrence of the start of an inspiratory event and the start of the next inspiratory event. In other words, the leak calculation is formed as an average over a known breath and applied to a subsequent breath.

This method cannot be used if the moment of start and end of the previous breath are unknown. In general, it can be difficult to accurately calculate the time of start of a breath. This is particularly the case immediately following a sudden change in the leak.

Furthermore, the method will not work in the case of a subject who is making no respiratory efforts, and is momentarily not being ventilated at all, for example during an apnea, because for the duration of the apnea there is no start or end of breath over which to make a calculation.

The present invention seeks to provide a determination of leak flow and true respiratory airflow, accounting for the variations in flow through a leak as a function of pressure.

SUMMARY OF THE INVENTION

The invention is a method for determining an instantaneous leak flow from a patient mask during mechanical ventilation including the acts of continuously determining values for pressure in the mask and airflow through the mask; calculating conductance of a leak as a function of the values for pressure and airflow determined over a time interval; and calculating the instantaneous leak flow as a function of the calculated leak conductance and the instantaneous determined value of mask pressure.

Embodiments of the invention provide advantages over the prior art. There is no need to know when transitions between respiratory phases occurs. The independence from knowledge of the subject's respiratory state has the important result that the leak flow calculation is accurate in apneic (i.e. no flow) instances on the part of the subject or the mechanical ventilator.

BRIEF DESCRIPTION OF THE DRAWINGS

Embodiments of the invention will now be described with reference to the accompanying drawings in which:

FIGS. 1a–1f shows traces of pressure and airflow from which respiratory airflow is calculated in accordance with a prior art method;

DETAILED DESCRIPTION OF PREFERRED EMBODIMENTS

Figure 2A:
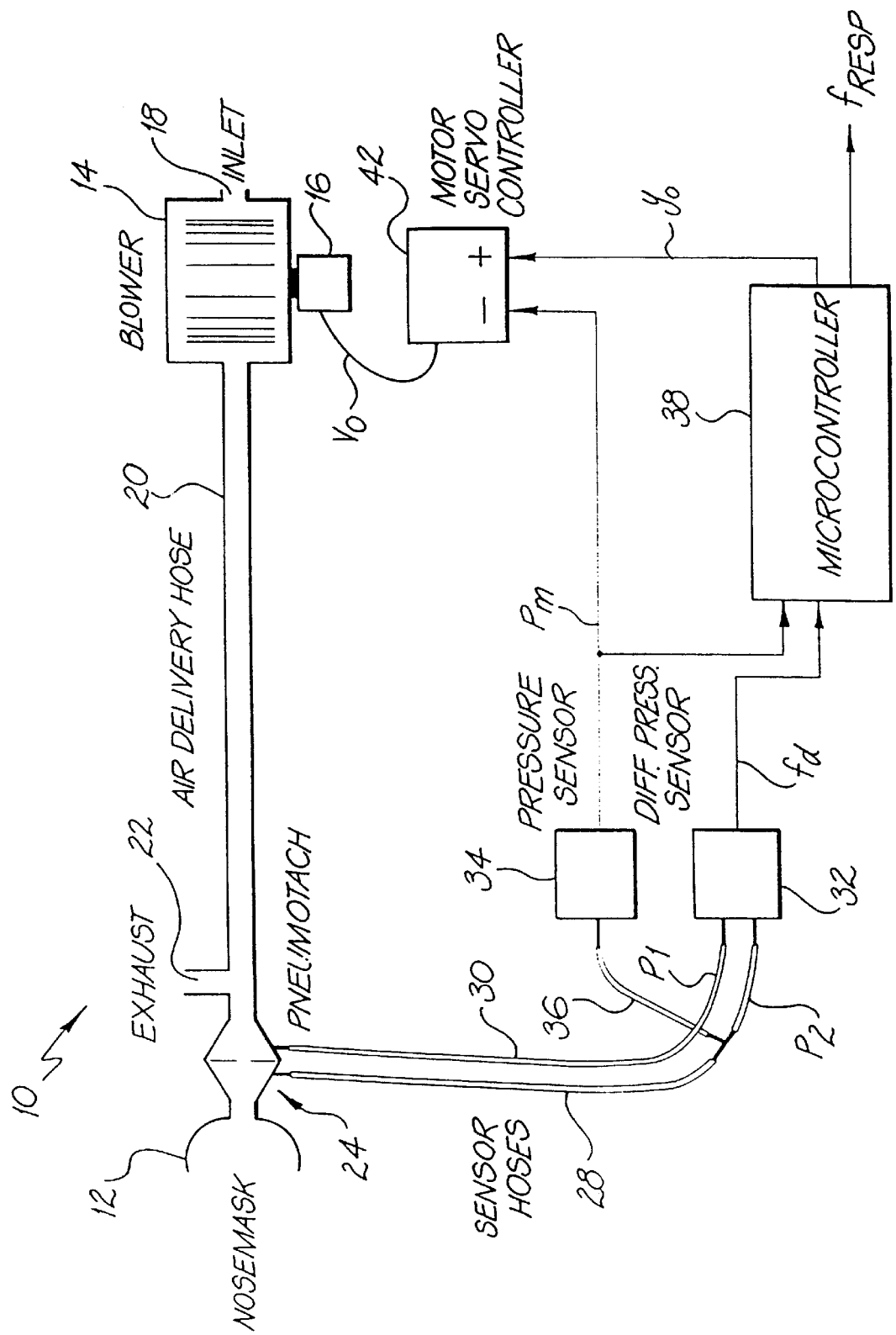
FIGS. 2a and b show schematic diagrams of two embodiments of ventilatory assistance apparatus.

FIG. 2a shows mechanical ventilation apparatus 10 embodying the invention.

The subject/patient wears a nose mask 12 of any known type. The subject equally could wear a face mask or nasal prongs/pillows, or alternatively have an endotracheal tube for tracheostomy tube in place. A turbine/blower 14, operated by a mechanically coupled electrical motor 16, receives air or breathable gas at an inlet 18 thereof, and supplies the breathable gas at a delivery pressure to a delivery tube/hose 20 having connection at the other end thereof with the nose mask 12. Breathable gas thus is provided to the subject's airway for the purpose of providing assisted respiration, with the subject's expired breath passing to atmosphere by an exhaust 22 in the delivery tube 20, typically located proximate to the mask 12.

A pneumotachograph 24 is placed in the delivery tube 20 between the mask 12 and the exhaust 22 to provide two pressure signals, $P_2$ and $P_1$, across the pneumotachograph, each passed by hoses 28,30 to a differential pressure sensor 32. A determination of the flow of gas in the mask 12 is made the differential pressure, $P_2-P_1$, resulting in a flow signal $f_d$. The mask pressure, $P_2$, also is passed to a pressure sensor 34 by a tapped line 36 taken from the respective hose 28, to generate a delivery pressure signal, $P_m$, output from the pressure senor 34.

Both the flow signal, $f_d$, and the pressure signal, $P_m$, are passed to a microcontroller 38 where they are sampled for subsequent signal processing, typically at a rate of 50 Hz.

The microcontroller 38 is programmed to process the flow and pressure signals ($f_d$, $P_m$) to produce an output control signal, $y_o$, provided to an electronic motor servo-controller 42 that, in turn, produces a motor speed control output signal, $v_o$. This signal is provided to the motor 16 to control the rotational speed of the turbine 14 and provide the desired treatment pressure, $P_2$, at the nose mask 12.

The motor servo-controller 42 employs a negative feedback control technique that compares the actual delivery pressure, in the form of the signal $P_m$, with the control signal $y_o$. For convenience, this control stratagem may be independent of operation of the microcontroller 38.

Operation of the controlling of the microcontroller 38, so far as a calculation of respiratory airflow is concerned, broadly is as follows. In a sampled manner, the conductance of any mask leak is calculated, then the instantaneous flow through the leak is calculated. The flow through the leak is subtracted from the total mask flow to calculate the true instantaneous respiratory airflow.

Figure 1A:
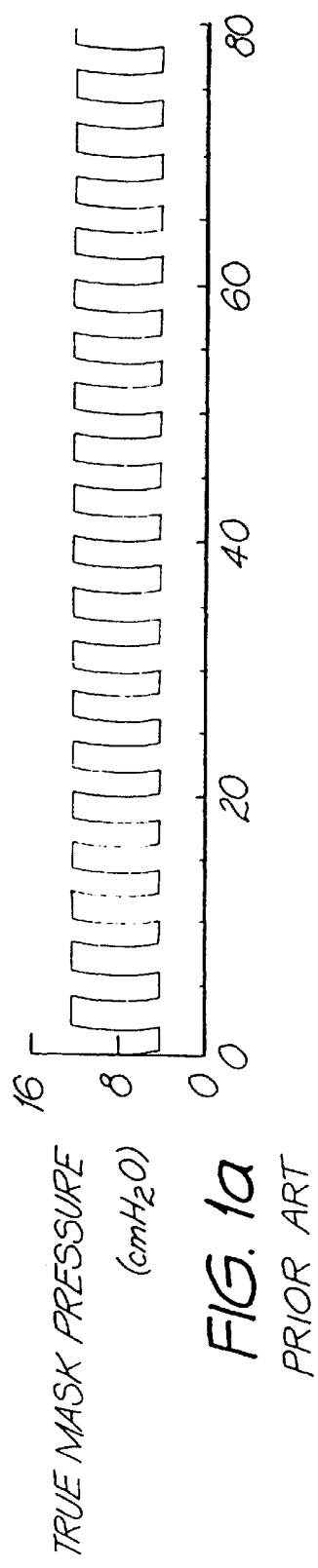
Figure 1B:
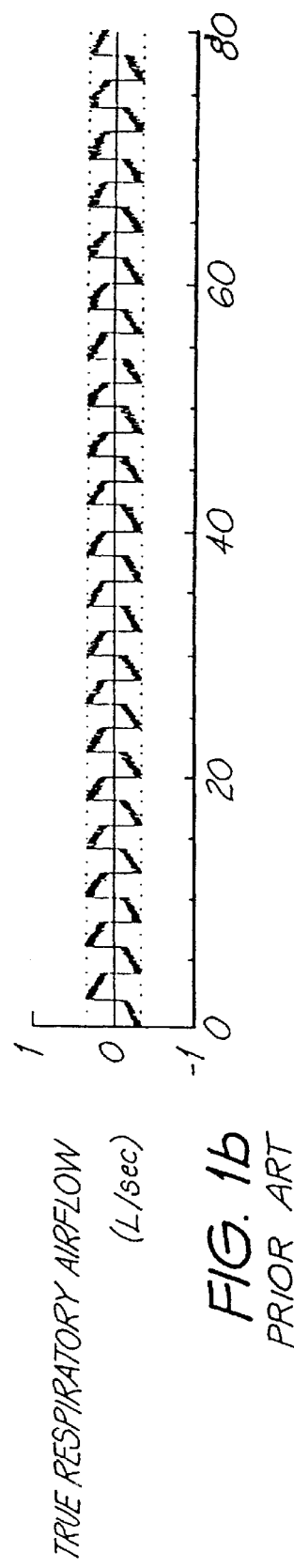
Figure 1C:
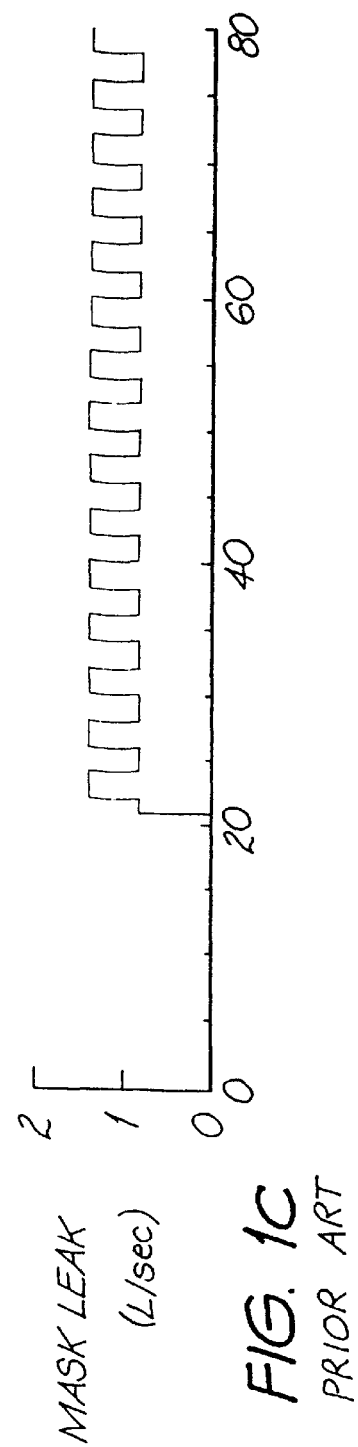
Figure 2B:
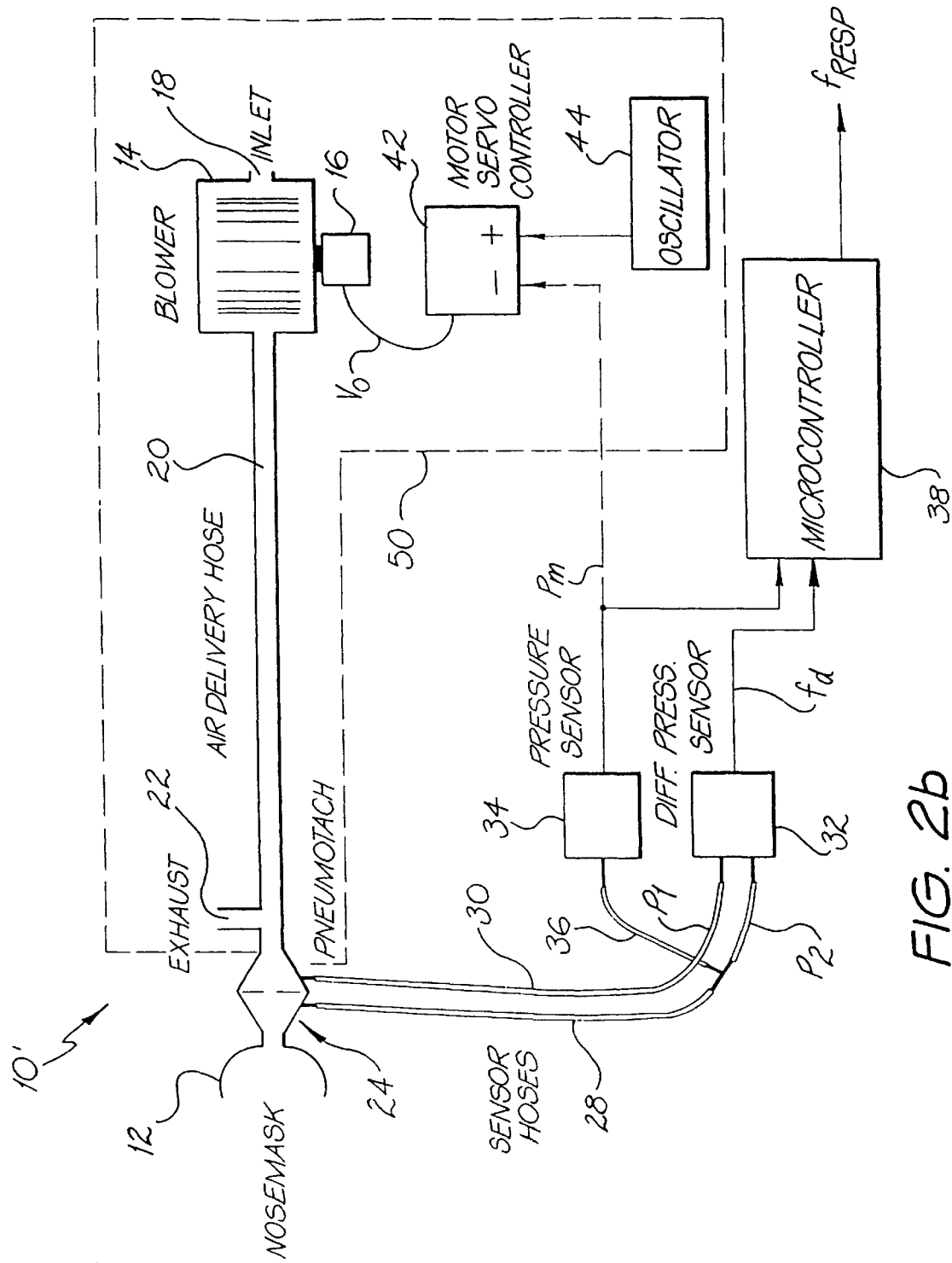

FIG. 2b shows an alternative embodiment of a system for determining true respiratory airflow during mechanical ventilation. The mechanical ventilation system 10 of FIG. 1b differs from that of FIG. 1a firstly in that the microcontroller 38 plays no part in control of the ventilator 50, rather only receives and data processes the electrically transduced mask pressure and flow signals $P_m$, $f_d$ to determine and generate the instantaneous respiratory flow $f_{RESP}$. The ventilator 50 has an internal drive signal provided by an oscillator 44. The motor servo controller also may or may not receive the mask pressure signal $P_m$ as a form of feedback control. Indeed, the ventilator 50 can be realized by any convenient form of known generic ventilation device.

Figure 3:
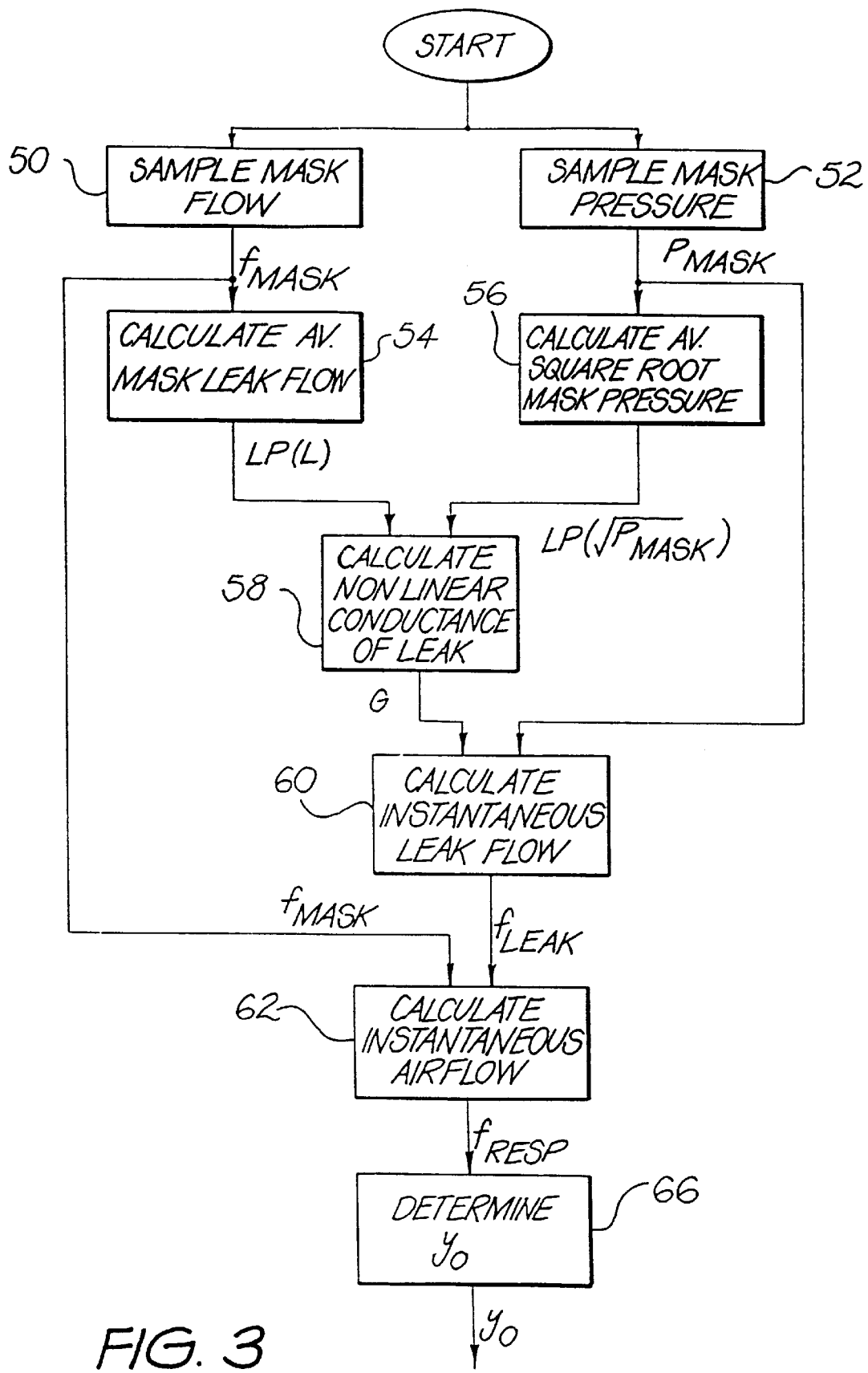
FIG. 3 is a block flow diagram of a method for determining instantaneous respiratory airflow.

The controlling software resident within the microcontroller 38 performs the following steps in determining the respiratory airflow as broadly described above, as also shown in the flow diagram of FIG. 3.

The word "average" is used herein in the most general sense of the result of a low pass filtering step, and is not confined to an arithmetic mean.

1. Repeatedly sample the mask airflow $f_d$ to give a sampled signal $f_{MASK}$, and the mask pressure $P_m$ to give a sampled signal $P_{MASK}$, for example at intervals of T=20 milliseconds. (Steps 50,52).
2. Calculate the average leak, LP(L), as being the result of low pass filtering the airflow, $f_{MASK}$, with a time constant of 10 seconds. (Step 54).
3. Calculate the average of the square root of the mask pressure, $LP(\sqrt{P_{MASK}})$, as being the result of low pass filtering the square root of the mask pressure, $P_{MASK}$, with a time constant of 10 seconds. (Step 56).
4. Calculate the conductance, G, of any leak (Step 58), from the equation:

$$G=LP(L)/LP(\sqrt{P_{MASK}})$$

5. Calculate the instantaneous leak flow, $f_{LEAK}$, through the leak (Step 60), from the equation:

$$f_{LEAK}=G\sqrt{\sqrt{P_{MASK}}}$$

If there is no leak flow, the value of LP(L) will be equal to zero, as will G and hence $f_{LEAK}$. Thus the methodology is valid also where leak is equal to zero—no leak.

At this juncture the leak flow has been determined, such as would be desired for a leak flow detector. If desired, the instantaneous respiratory airflow can be subsequently determined by the following step.

6. Calculate the instantaneous respiratory airflow, $f_{RESP}$, by subtracting the instantaneous leak from the mask flow (Step 62):

$$f_{RESP}=f_{MASK}-f_{LEAK}$$

Figure 4A:
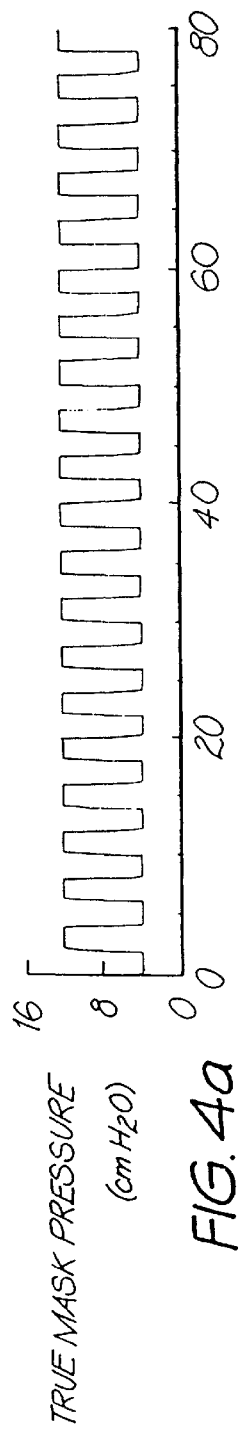
FIG. 4 shows traces of pressure, airflow and other variables from which respiratory airflow is calculated.
Figure 4B:
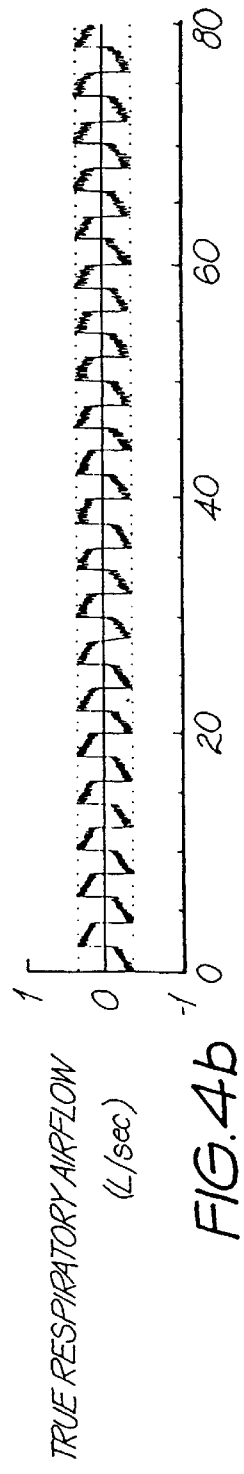
Figure 4C:
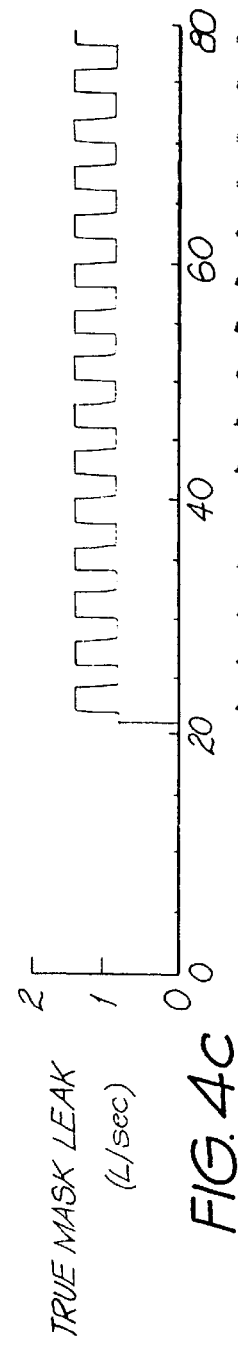
Figure 4D:
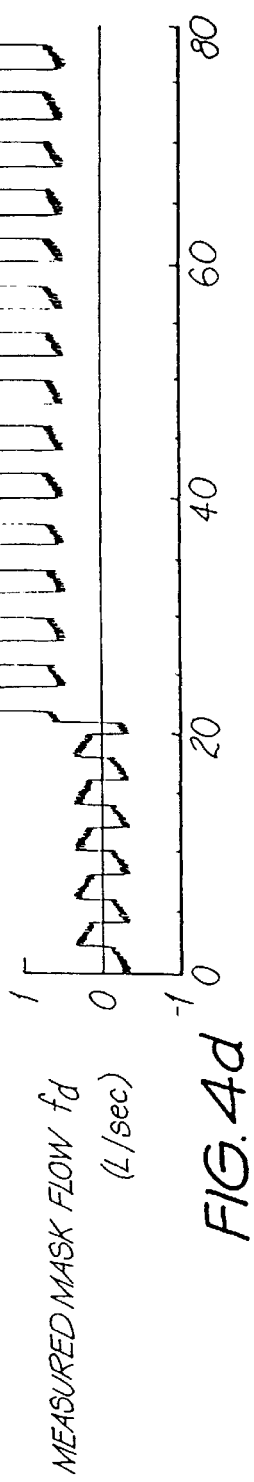
Figure 4E:
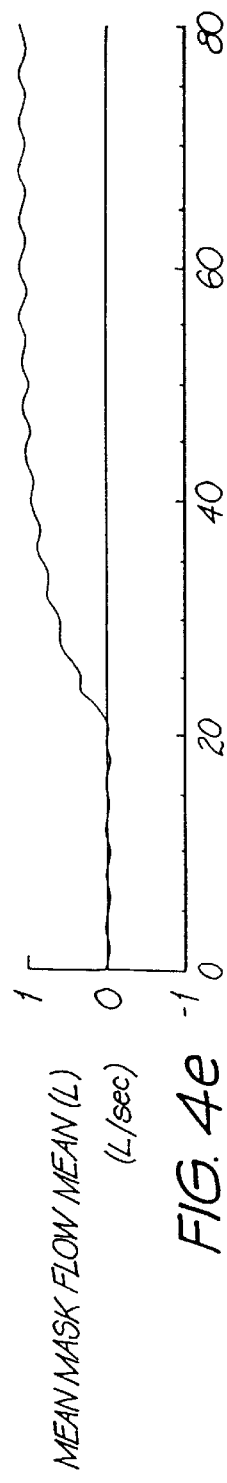
Figure 4F:
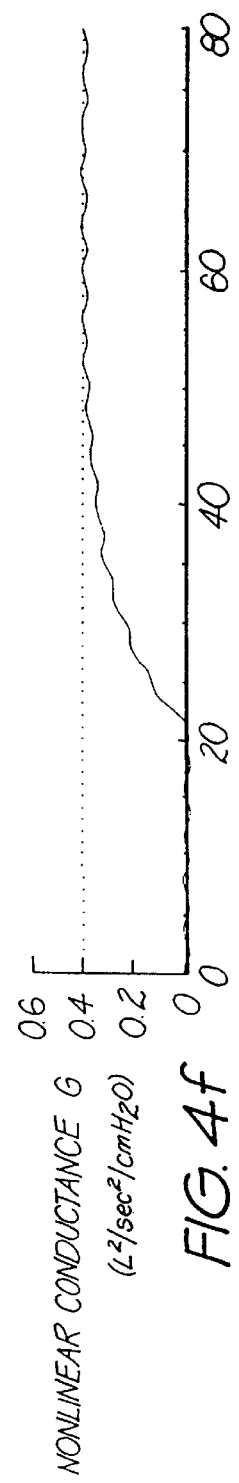
Figure 4G:
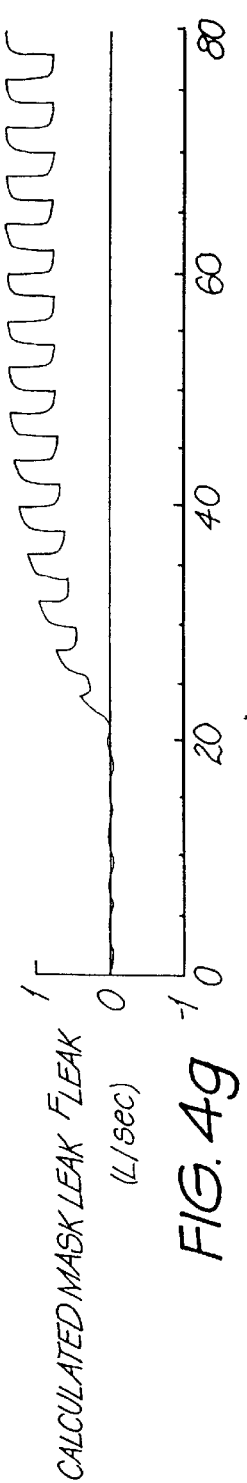
Figure 4H:
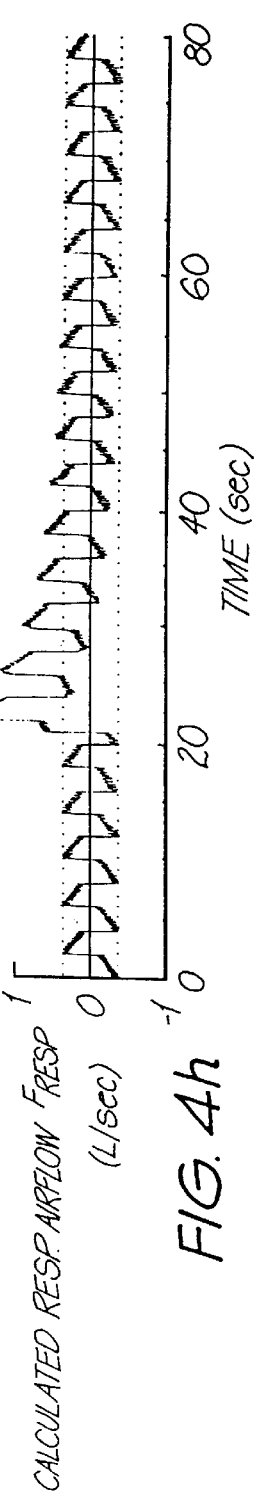

FIGS. 4a–4h illustrate the methodology of the embodiment described above with reference to FIG. 2b. At time, t32 21 sec, a continuing leak of approximately 1l/sec is introduced. FIG. 4e shows the mean mask flow. FIG. 4f represents the calculated conductance G, from which the mask leak flows can be estimated as shown in FIG. 4g. Finally, FIG. 4h shows how the calculated respiratory airflow recovers within approximately 30 seconds, and, importantly, gives the correctly scaled (true) magnitude of airflow.

With regard to setting the instantaneous output signal $y_o$, the microcontroller broadly executes the following steps: 7. If the calculated true respiratory airflow $f_{RESP}$ is above a threshold, for example 0.05 L/sec. $y_o$ is set to a value corresponding to an inspiratory pressure. $P_{INSP}$. Otherwise $y_o$ is set to a value corresponding to an expiratory pressure. $P_{EXP}$. In general, $P_{INSP}$ is higher than $P_{EXP}$, but in the case of continuous positive airways pressure, $P_{EXP}$ may be equal to $P_{INSP}$, (Step 66).

It is to be understood that many other methods of determining $y_o$ from $f_{MASK}$ may be used in step 7, for example as described in the text *Principles and Practice of Mechanical Ventilation*, edited by Martin J. Tobin (McGraw Hill Inc, 1994).

In order to control ventilation, it is necessary to measure the subject's ventilation. In the presence of a leak, the ventilation delivered by the assisted ventilation apparatus is greater than the ventilation delivered to the subject. Known devices which servo-control ventilation cope with this by collecting the exhaled air stream with a complex system of valves, and then measuring the exhaled ventilation. This is inappropriate for devices for use in a domestic setting during sleep, because of the attendant weight, complexity, and expense. The embodiment described compensates for the leak by continuously measuring the nonlinear conductance of the leak, and allowing for the instantaneous flow through the leak as a function of pressure.

Figure 5:
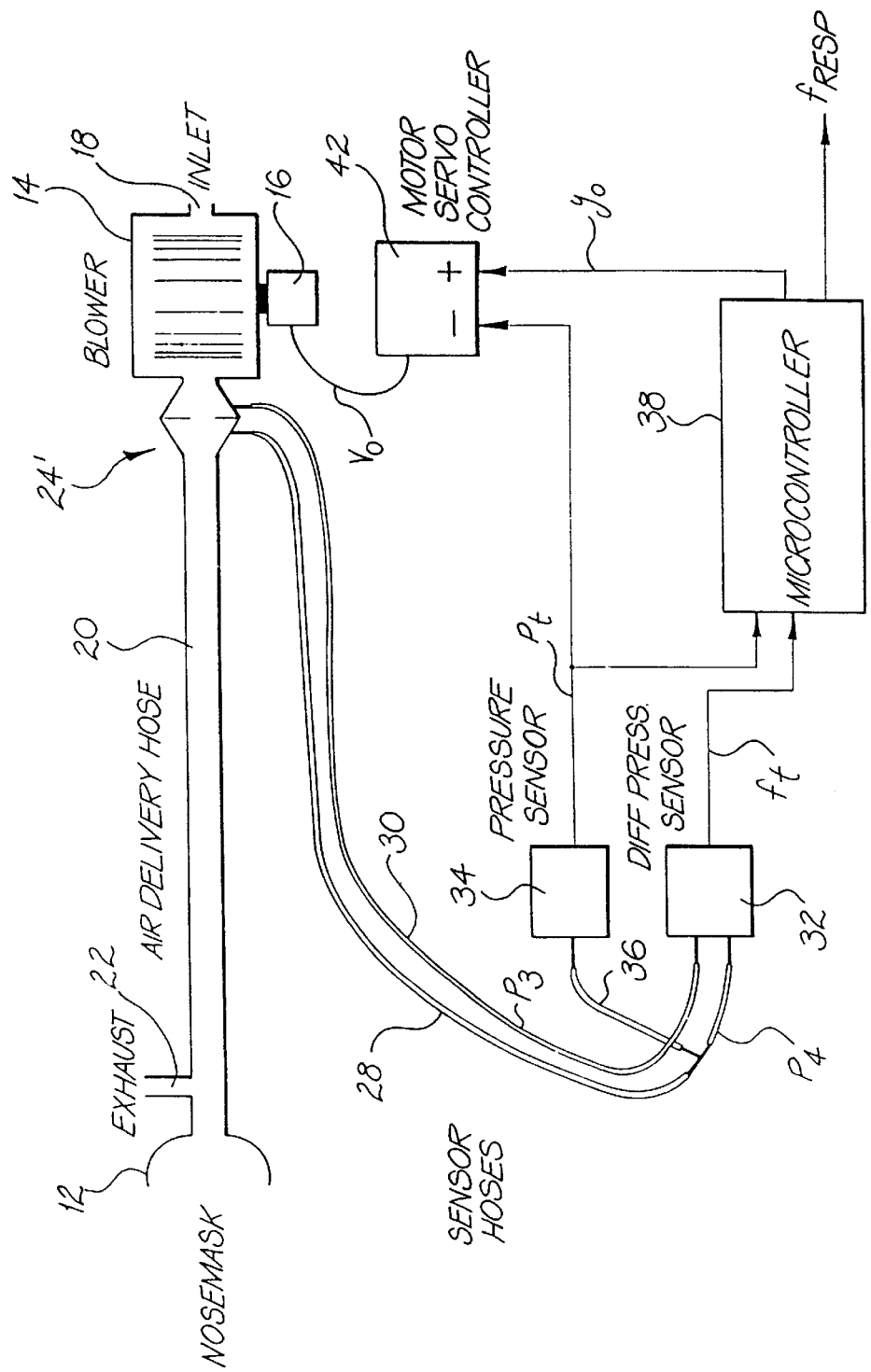
FIG. 5 shows a schematic diagram of ventilatory assistance apparatus of another embodiment.

FIG. 5 shows an alternate arrangement for ventilatory assistance apparatus 10' embodying the invention. In this arrangement, the pneumotachograph 24' is interposed between the turbine 14 and the delivery hose 20.

This arrangement removes the pressure sensing hoses and pneumotachograph from the region of the mask 12. The pressure at the mask, $P_{MASK}$, is calculated from the delivery pressure at the turbine 14, and from the pressure drop down the air delivery hose 20, which for any particular delivery hose is a known function of the flow at the pneumotachograph 24. Further, the microcontroller 38 must also calculate the flow through the mask from the flow at the turbine 14 less the flow through the exhaust 22, which for any particular exhaust is a known function of the pressure at the mask 12.

In more detail, this involves the step of, firstly measuring the pressure $P_3$ at the turbine 14 with the pressure sensor 34 to produce an electrical signal $P_t$. Next the differential pressure $P_4-P_3$ is measured across the pneumotachograph 24' by the differential pressure sensor 32 to produce an electrical signal $f_t$. In a sampled manner, $P_t$ and $f_t$ are digitized to yield the sampled turbine pressure and flow signals $P_{TURBINE}$ and $F_{TURBINE}$.

The pressure at the mask $P_{MASK}$ and the sampled airflow at the mask $f_{MASK}$ 12 are calculated from the turbine pressure $P_{TURBINE}$ and the flow at the outlet of the turbine $F_{TURBINE}$ as follows:

1. Calculate the pressure drop $\Delta P_{TUBE}$ down the air delivery tube 20, from the flow at the outlet of the turbine $F_{TURBINE}$:

$$\Delta P_{TUBE}=sign(F_{TURBINE}) \times K_1(F_{TURBINE})^2+K_2 F_{TURBINE}$$

where $K_1$ and $K_2$ are empirically determined constants, and sign ($\chi$) is 1 for $\chi \geq 0$ and −1 otherwise.

2. Calculate the pressure at the mask, $P_{MASK}$, as the pressure at the turbine $P_{TURBINE}$ less the pressure drop $\Delta P_{TUBE}$ down the air delivery tube 20:

$$P_{MASK}=P_{TURBINE}-\Delta P_{TUBE}$$

3. Calculate the flow, $f_{EXHAUST}$, though the exhaust 22, from the pressure at the mask $P_{MASK}$:

$$f_{EXHAUST}=sign(P_{MASK}) \times K_3 \sqrt{\sqrt{abs(P_{MASK})}}$$

where $K_3$ is determined empirically.

4. Calculate the flow, $f_{MASK}$, into the mask 12 as the flow at the turbine 14 less the flow through the exhaust 22:

$$f_{MASK}=f_{TURBINE}-f_{EXHAUST}$$

The foregoing embodiments describe low-pass filtering of both the instantaneous airflow and the square root of the instantaneous pressure with a time constant $\tau$ of 10 seconds. This time constant, $\tau$, can be advantageously dynamically adjustable.

If the conductance of the leak suddenly changes, then the calculated conductance will initially be incorrect, and will gradually approach the correct value at a rate which will be slow if the time constant of the low pass filters is long, and fast if the time constant is short. Conversely, if the impedance of the leak is steady, the longer the time constant the more accurate the calculation of the instantaneous leak. Therefore, it is desirable to lengthen the time constant if it is certain that the leak is steady, reduce the time constant if it is certain that the leak has suddenly changed, and to use intermediately longer or shorter time constants if it is intermediately certain that the leak is steady.

If there is a large and sudden increase in the conductance of the leak, then the calculated respiratory airflow will be incorrect. In particular during apparent inspiration, the calculated respiratory airflow will be large positive for a time that is large compared with the expected duration of a normal inspiration. Conversely, if there is a sudden decrease in conductance of the leak, then during apparent expiration the calculated respiratory airflow will be large negative for a time that is large compared with the duration of normal expiration.

Therefore, an index of the degree of certainty that the leak has suddenly changed is derived, such that the longer the airflow has been away from zero, and by a larger amount, the larger the index; and the time constant for the low pass filters is adjusted to vary inversely with the index. In operation, if there is a sudden and large change in the leak, the index will be large, and the time constant for the calculation of the conductance of the leak will be small, allowing rapid convergence on the new value of the leakage conductance. Conversely, if the leak is steady for a long time, the index will be small, and the time constant for calculation of the leakage conductance will be large, enabling accurate calculation of the instantaneous respiratory airflow. In the spectrum of intermediate situations, where the calculated instantaneous respiratory airflow is larger and for longer periods, the index will be progressively larger, and the time constant for the calculation of the leak will progressively reduce. For example, at a moment in time where it is uncertain whether the leak is in fact constant, and the subject merely commenced a large sigh, or whether in fact there has been a sudden increase in the leak, the index will be of an intermediate value, and the time constant for calculation of the impedance of the leak will also be of an intermediate value. One advantage is that some corrective action will occur very early.

Another advantage is that there is never a moment where the leak correction algorithm is "out of control" and needs to be restarted, as described for prior art European Patent Publication No. 0 714 670 A2.

Figure 6:
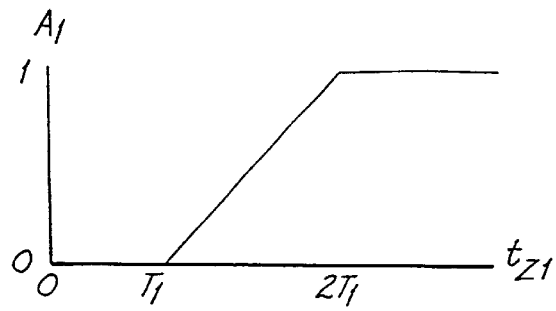
FIG. 6 shows a fuzzy membership function for the calculation of the extent $A_I$ to which the time $t_{ZI}$ since the most recent positive going zero crossing of the calculated respiratory airflow is longer than the expected time $T_1$.
Figure 7:
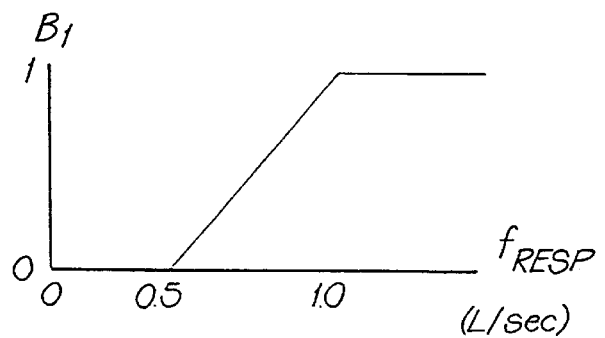
FIG. 7 shows a fuzzy membership function for the calculation of the extent $B_t$ to which the calculated inspiratory respiratory airflow $f_{RESP}$ is large positive.

In a preferred embodiment, the above index is derived using fuzzy logic. The fuzzy extent $A_I$ to which the airflow has been positive for longer than expected is calculated from the time $t_{ZI}$ since the last positive-going zero crossing of the calculated respiratory airflow signal, and the expected duration $T_I$ of a normal inspiration for the particular subject, using the fuzzy membership function shown in FIG. 6. The fuzzy extent $B_I$ to which the airflow is large and positive is calculated from the instantaneous respiratory airflow using the fuzzy membership function shown in FIG. 7. The instantaneous index $I_I$ of the degree of certainty that the leak has suddenly increased is calculated as the fuzzy intersection (lesser) of $A_I$ and $B_I$.

Figure 8:
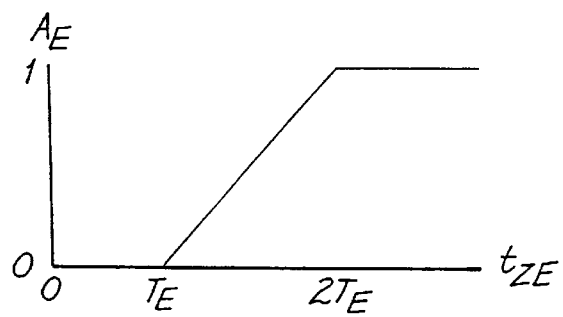
FIG. 8 shows a fuzzy membership function for the calculation of the extent $A_B$ to which the time $t_{ZE}$ since the most recent negative going zero crossing in the calculated respiratory airflow is longer than the expected time $T_B$.
Figure 9:
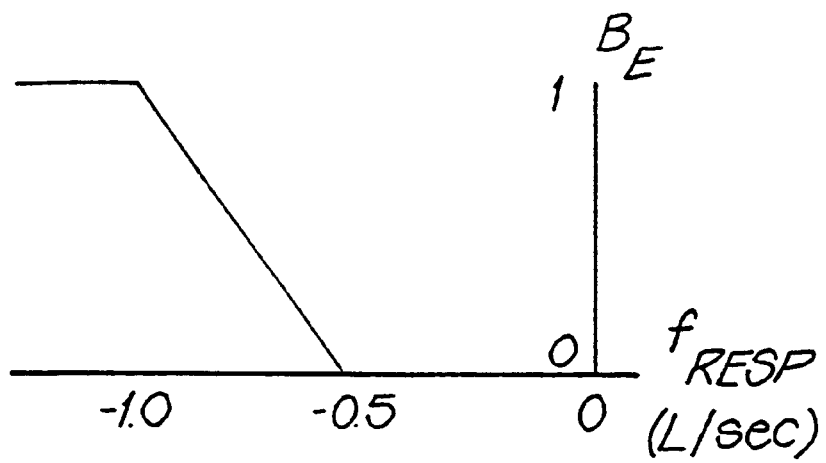
FIG. 9 shows a fuzzy membership function for the calculation of the extent $B_E$ to which the respiratory airflow $f_{RESP}$ is large negative.

Comparable calculations are performed for expiration as follows. The fuzzy extent $A_E$ to which the airflow has been negative for longer than expected is calculated from the time $t_{ZE}$ since the last negative-going zero crossing of the calculated respiratory airflow signal, and $T_B$, the expected duration of a typical expiration for the particular subject, using the membership function shown in FIG. 8. The fuzzy extent $B_E$ to which the airflow is large negative is calculated from the instantaneous respiratory airflow using the fuzzy membership function shown in FIG. 9. The instantaneous index $I_E$ of the degree of certainty that the leak has suddenly decreased is calculated as the fuzzy intersection of $A_E$ and $B_E$.

Figure 10:
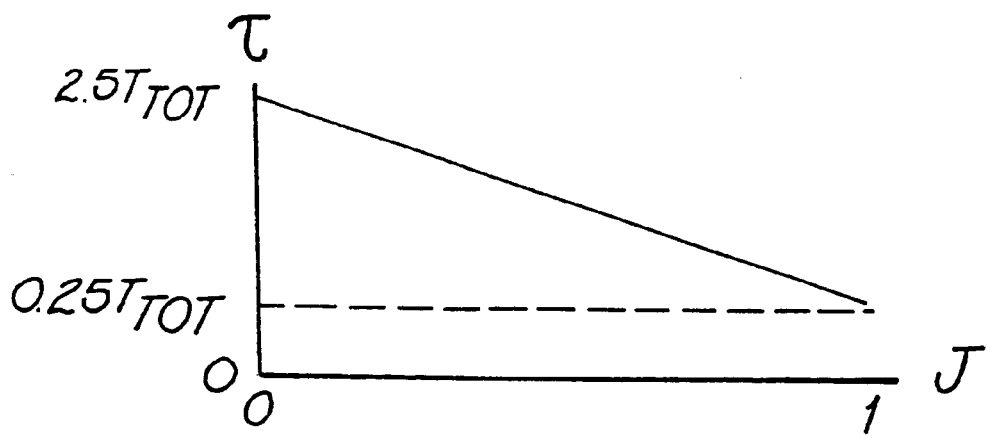
FIG. 10 shows the relation between the index J and time constant $\tau$.

The instantaneous index I of the extent to which there has been a sudden change in the leak (either an increase or a decrease) is calculated as the fuzzy union (larger) of indices $I_I$ and $I_E$. The instantaneous index I is then passed through a peak detector followed by a low pass filter with a time constant of, for example 2 seconds, to yield the desired index J. Thus if index I becomes momentarily large, index J will be initially large and remain so for a few seconds. The time constant τ for the low pass filters used in the calculation of the conductance of the leak is then adjusted to vary inversely with the index J, as shown in FIG. 10. For example, if the expected duration of a normal respiratory cycle were 4 seconds the time constant is set to 10 seconds if the index J is zero, (corresponding to complete certainty that the leak is steady), and to 1 second if the index J is unity (corresponding to complete certainty that the leak is suddenly changing), and to intermediate values for intermediate cases.

The embodiments described refer to apparatus for the provision of ventilatory assistance, however, it is to be understood that the invention is applicable to all forms of mechanical ventilation and apparatus for the provision of continuous positive airway pressure treatment. The apparatus can be for the provision of a constant treatment pressure, multi-level (IPAP and EPAP) treatment or autosetting (adjusting) treatment or other forms of mechanical ventilation, including Proportional Assist Ventilation (PAV) as taught by M Younes in the above-noted text.

The methodology described can be implemented in the form of a computer program that is executed by the microcontroller described, or by discrete combinational logic elements, or by anolog hardware.

What is claimed is:

1. A method for determining the instantaneous leak flow from a face mask comprising the steps of:
   (a) determining pairs of values for pressure in the mask and airflow through the mask;
   (b) calculating the conductance of a leak as a function of pairs of values for pressure and airflow that are determined over a time interval that exceeds a normal breath; and
   (c) calculating the instantaneous leak flow as a function of the calculated leak conductance and an instantaneous determined value of mask pressure.

2. A method in accordance with claim 1 wherein said pairs of values are determined by taking direct measures of pressure and airflow.

3. A method in accordance with claim 1, accomplished by apparatus that includes an air delivery system, wherein said pairs of values are determined by taking direct measures of pressure and airflow in said air delivery system at a point remote from said face mask, and calculating said pairs of values in accordance with physical characteristics of said air delivery system and said direct measures.

4. A method in accordance with claim 1, 2 or 3 wherein said time interval varies as a function of the rate at which the calculated leak conductance changes.

5. A method in accordance with claims 1, 2 or 3 wherein said time interval varies inversely with the rate at which the calculated leak conductance changes.

6. Apparatus for determining the instantaneous leak flow from a patient mask during mechanical ventilation comprising transducer means located at or approximate to the mask to determine instantaneous values for the pressure in the mask and the airflow through the mask; and processor means for calculating the conductance of the leak as a function of said pressure and airflow values determined over a time interval exceeding that of a normal breath, and for calculating the instantaneous leak flow as a function of the calculated leak conductance and the instantaneously determined value of mask pressure.

7. The apparatus of claim 6 wherein said transducer means determines said instantaneous values by taking direct measures of mask pressure and airflow.

8. The apparatus of claim 7 wherein said processor means varies said time interval over which pressure and airflow values are used to determine leak conductance in accordance with the rate at which the calculated leak conductance changes.

9. The apparatus of claim 7 wherein said processor means varies said time interval over which pressure and airflow values are used to determine leak conductance inversely with the rate at which the calculated leak conductance changes.

10. Apparatus for providing mechanical ventilation for a patient comprising a flow generator for the supply of pressurized breathable gas; a gas delivery system having connection with the flow generator; a mask having connection with the gas delivery system to supply said gas to the airway of said patient; transducer means continuously taking measurements from which the pressure in the mask and the airflow through the mask can be determined; processor means calculating the conductance of any mask leak as a function of said mask pressure and airflow values determined over a time interval exceeding that of a normal breath, and for calculating the instantaneous leak flow as a function of the calculated leak conductance and the determined value of mask pressure; and control means to adjust said flow generator to control at least one of mask pressure and mask airflow on the basis of the mask airflow and calculated leak flow.

11. The apparatus of claim 10 wherein the transducer means takes direct measures of mask pressure and airflow.

12. The apparatus of claim 10 wherein said transducer means takes direct measures of pressure and airflow in said gas delivery system at a point remote from the mask, and said processor means calculates mask pressure and airflow values in accordance with physical characteristics of said gas delivery system and said direct measures.

13. The apparatus of claim 11 or claim 12 wherein said processor means varies said time interval over which pressure and airflow values are used to determine leak conductance in accordance with the rate at which the calculated leak conductance changes.

14. The apparatus of claim 11 or claim 12 wherein said processor means varies said time interval over which pressure and airflow values are used to determine leak conductance inversely with the rate at which the calculated leak conductance changes.

15. A method for determining the instantaneous leak flow from a patient mask comprising the steps of determining instantaneous values for pressure in the mask and airflow through the mask; calculating the conductance of the leak as a function of the average values of the respective pressure and airflow instantaneous values wherein said average values are taken over a period exceeding a normal breath; and calculating the instantaneous leak flow as a function of the calculated leak conductance and the instantaneously determined value of mask pressure.

16. The method of claim 15 wherein the time interval over which pressure and airflow values are used to determine leak conductance is varied in accordance with the rate at which the calculated leak conductance changes.

17. The method of claim 15 wherein the time interval over which pressure and airflow values are used to determine leak conductance is varied inversely with the rate at which the calculated leak conductance changes.

18. A method of providing breathable gas for a patient comprising the steps of supplying pressurized breathable gas via a mask to the airway of said patient; continuously taking measurements from which the pressure in the mask and the airflow through the mask can be determined; calculating the conductance of any mask leak as a function of said mask pressure and airflow values determined over a time interval exceeding that of a normal breath, and calculating the instantaneous leak flow as a function of the calculated leak conductance and the determined value of mask pressure; and adjusting the supply of said breathable gas in accordance with the mask airflow and calculated leak flow.

19. The method of claim 18 wherein direct measures of pressure and airflow are taken.

20. The method of claim 18 wherein direct measures of pressure and airflow are taken at a point remote from the mask, and mask pressure and airflow values are calculated in accordance with said direct measures and physical characteristics of the air delivery system over which said breathable gas is supplied to the airway of the patient.

21. The method of claim 19 or claim 20 wherein the time interval over which pressure and airflow values are used to determine leak conductance is varied in accordance with the rate at which the calculated leak conductance changes.

22. The method of claim 19 or claim 20 wherein the time interval over which pressure and airflow values are used to determine leak conductance is varied inversely with the rate at which the calculated leak conductance changes.

23. Apparatus for determining the instantaneous leak flow from a patient mask comprising means for determining instantaneous values for the pressure in the mask and the airflow through the mask; means for calculating the conductance of the leak as a function of the average values of the respective pressure and airflow instantaneous values taken over a time period of more than a normal breath; and means for calculating the instantaneous leak flow as a function of the calculated leak conductance and an instantaneously determined value of pressure in the mask.

24. Apparatus in accordance with claim 23 wherein the time interval over which pressure and airflow values are used to determine leak conductance is varied in accordance with the rate at which the calculated leak conductance changes.

25. Apparatus for determining the instantaneous leak flow from a patient mask comprising means for determining instantaneous values for pressure in the mask and airflow through the mask; means for calculating the conductance of the leak as a function of the average values of the respective pressure and airflow instantaneous values; and means for calculating the instantaneous leak flow as a function of the calculated leak conductance and an instantaneously determined value of pressure in the mask, wherein the time interval over which pressure and airflow values are used to determine leak conductance is varied inversely with the rate at which the calculated leak conductance changes.

26. Apparatus for providing breathable gas to a patient comprising means for supplying pressurized breathable gas via a mask to the airway of said patient; means for continuously taking measurements from which the pressure in the mask and the airflow through the mask can be determined; means for calculating the conductance of any mask leak as a function of said mask pressure and airflow values determined over a time interval exceeding that of a normal breath, and for calculating the instantaneous leak flow as a function of the calculated leak conductance and the determined value of mask pressure; and means for adjusting the supply of said breathable gas in accordance with the mask airflow and calculated leak flow.

27. Apparatus in accordance with claim 26 wherein direct measures of pressure and airflow are taken.

28. Apparatus in accordance with claim 26 wherein direct measures of pressure and airflow are taken at a point remote from the mask, and mask pressure and airflow values are calculated in accordance with said direct measures and physical characteristics of said gas supplying means.

29. Apparatus in accordance with claim 27 or claim 28 wherein the time interval over which pressure and airflow values are used to determine leak conductance is varied in accordance with the rate at which the calculated leak conductance changes.

30. Apparatus in accordance with claim 28 or claim 29 wherein the time interval over which pressure and airflow values are used to determine leak conductance is varied inversely with the rate at which the calculated leak conductance changes.

31. A method for determining an instantaneous leak flow from a patient mask during mechanical ventilation comprising the step of:
(a) continuously determining values for pressure in the mask and airflow through the mask wherein said values are determined by taking direct measures of pressure and airflow;
(b) calculating conductance of a leak as a function of the values for pressure and airflow determined over a time interval wherein said time interval exceeds that of a normal breath and varies inversely with the rate at which the calculated leak conductance changes; and
(c) calculating the instantaneous leak flow as a function of the calculated leak conductance and an instantaneous determined value of mask pressure.

32. A method for determining an instantaneous leak flow from a patient mask during mechanical ventilation from an air delivery system comprising the steps of:
(a) continuously determining values for pressure in the mask and airflow through the mask wherein said values are determined by taking direct measures of pressure and airflow at a point remote from the mask and calculating said values in accordance with physical characteristics of the air delivery system and the direct measures;
(b) calculating conductance of a leak as a function of the values for pressure and airflow determined over a time interval wherein said time interval exceeds that of a normal breath and varies inversely with the rate at which the calculated leak conductance changes; and
(c) calculating the instantaneous leak flow as a function of the calculated leak conductance and an instantaneous determined value of mask pressure,
wherein said mechanical ventilation is accomplished by forcing air to flow through the air delivery system.

33. A method for determining the instantaneous leak flow from a patient mask comprising the steps of determining instantaneous values for pressure in the mask and airflow through the mask; calculating the conductance of the leak as a function of the average values of the respective pressure and airflow instantaneous values; and calculating the instantaneous leak flow as a function of the calculated leak conductance and an instantaneously determined value of mask pressure, wherein the time interval over which pressure and airflow values are used to calculate leak conductance is varied inversely with the rate at which the calculated leak conductance changes.

* * * * *